United States Patent
Behnke, II

(10) Patent No.: US 9,987,069 B2
(45) Date of Patent: *Jun. 5, 2018

(54) SYSTEM AND METHOD FOR MEASURING CURRENT OF AN ELECTROSURGICAL GENERATOR

(71) Applicant: COVIDIEN LP, Mansfield, MA (US)

(72) Inventor: Robert J. Behnke, II, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 371 days.

This patent is subject to a terminal disclaimer.

(21) Appl. No.: 14/692,249

(22) Filed: Apr. 21, 2015

(65) Prior Publication Data
US 2015/0223858 A1    Aug. 13, 2015

Related U.S. Application Data

(63) Continuation of application No. 12/985,063, filed on Jan. 5, 2011, now Pat. No. 9,028,481.

(51) Int. Cl.
*A61B 18/00* (2006.01)
*A61B 18/12* (2006.01)
*A61B 18/14* (2006.01)

(52) U.S. Cl.
CPC .......... *A61B 18/00* (2013.01); *A61B 18/1233* (2013.01); *A61B 18/1477* (2013.01); *A61B 2018/0072* (2013.01); *A61B 2018/00648* (2013.01); *A61B 2018/00702* (2013.01); *A61B 2018/00791* (2013.01); *A61B 2018/00875* (2013.01)

(58) Field of Classification Search
CPC .......... A61B 18/00; A61B 2018/00702; A61B 2018/0072

USPC .............................................. 606/34, 38, 41
See application file for complete search history.

(56) References Cited

U.S. PATENT DOCUMENTS

| | | |
|---|---|---|
| 3,897,787 A | 8/1975 | Ikuno et al. |
| 3,938,040 A | 2/1976 | Lofmark |
| 3,946,738 A | 3/1976 | Newton et al. |
| 4,188,927 A | 2/1980 | Harris |
| 4,378,801 A | 4/1983 | Oosten |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

International Search Report EP10150563.4 dated Jun. 10, 2010.

(Continued)

*Primary Examiner* — Christopher D Koharski
*Assistant Examiner* — Roland Dinga

(57) ABSTRACT

An electrosurgical generator includes an RF output stage, a DC blocking capacitor, a measuring circuit, and a sensor circuit. The RF output stage generates electrosurgical energy for application to an active electrode. The DC blocking capacitor is electrically coupled between the RF output stage and the active electrode. The measuring circuit is coupled to the DC blocking capacitor and measures the voltage across the DC blocking capacitor. The sensor circuit determines the current of the electrosurgical energy as a function of the voltage across the DC blocking capacitor.

15 Claims, 2 Drawing Sheets

(56) References Cited

U.S. PATENT DOCUMENTS

| | | | |
|---|---|---|---|
| 4,767,999 A | 8/1988 | VerPlanck | |
| 4,788,634 A | 11/1988 | Schlecht et al. | |
| 4,788,977 A | 12/1988 | Farin et al. | |
| 4,931,717 A | 6/1990 | Gray et al. | |
| 4,969,885 A | 11/1990 | Farin | |
| 4,992,719 A | 2/1991 | Harvey | |
| 5,300,070 A * | 4/1994 | Gentelia | A61B 17/3462 604/164.11 |
| 6,104,248 A | 8/2000 | Carver | |
| 6,547,786 B1 | 4/2003 | Goble | |
| 6,939,347 B2 | 9/2005 | Thompson | |
| 7,195,627 B2 | 3/2007 | Amoah et al. | |
| 7,211,081 B2 | 5/2007 | Goble | |
| D574,323 S | 8/2008 | Waaler | |
| 9,028,481 B2 | 5/2015 | Behnke, II | |
| 2004/0030328 A1 | 2/2004 | Eggers et al. | |
| 2004/0095100 A1 | 5/2004 | Thompson | |
| 2009/0082765 A1 | 3/2009 | Collins et al. | |
| 2010/0063494 A1* | 3/2010 | Orszulak | 606/33 |
| 2010/0063497 A1 | 3/2010 | Orszulak | |
| 2011/0071521 A1 | 3/2011 | Gilbert | |
| 2011/0087256 A1 | 4/2011 | Wiener et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3604823 A1 | 12/1982 |
| DE | 3510598 A1 | 10/1986 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2474282 A2 | 7/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 2146534 A | 4/1985 |
| JP | 49-89392 | 8/1974 |
| JP | 08-233884 | 9/1996 |
| SU | 166452 | 1/1965 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 20061050888 A1 | 5/2006 |
| WO | 2008053532 A1 | 5/2008 |

OTHER PUBLICATIONS

International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10191319.2 dated Feb. 22, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Japanese Office Action dated May 8, 2015 for JP 2011-289446.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.

(56) References Cited

OTHER PUBLICATIONS

International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
Japanese Notice of Allowance for JP 2011-289446 dated Dec. 1, 2015.
European Search Report for European Application No. 12150263.7 dated Jun. 1, 2012.
Extended European Search Report dated Apr. 2, 2014 for EP 14 15 2809.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/566,173, filed Sep. 24, 2009, James A. Gilbert.
U.S. Appl. No. 12/566,233, filed Sep. 24, 2009, William N. Gregg.
U.S. Appl. No. 12/567,966, filed Sep. 28, 2009, Craig A. Keller.
U.S. Appl. No. 12/613,876, filed Nov. 6, 2009, Craig A. Keller.
U.S. Appl. No. 12/619,234, filed Nov. 16, 2009, James A. Gilbert.
U.S. Appl. No. 12/639,210, filed Dec. 16, 2009, Jennifer S. Harper.
U.S. Appl. No. 12/712,712, filed Feb. 25, 2010, Mani N. Prakash.
U.S. Appl. No. 12/713,956, filed Feb. 26, 2010, Robert B. Smith.
U.S. Appl. No. 12/715,212, filed Mar. 1, 2010, Robert J. Behnke, II.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
Canadian Office Action dated Oct. 23, 2017 in corresponding Canadian Patent Application No. 2,763,152, 4 pages.

* cited by examiner

SYSTEM AND METHOD FOR MEASURING CURRENT OF AN ELECTROSURGICAL GENERATOR

CROSS-REFERENCE TO RELATED APPLICATIONS

This application is a continuation of U.S. patent application Ser. No. 12/985,063, filed on Jan. 5, 2011, the entire disclosure of which is incorporated by reference herein.

BACKGROUND

Technical Field

The present disclosure relates to a system and method for performing electrosurgical procedures. More particularly, the present disclosure relates to a system and method for measuring current of an electrosurgical generator using the voltage across a DC blocking capacitor.

Background of Related Art

Electrosurgery involves application of radio frequency electrical current (e.g., electrosurgical energy) to a surgical site to cut, ablate, coagulate, or seal tissue. The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, usually causing current to flow through a small amount of tissue. In monopolar electrosurgery, the return electrode is located elsewhere on the patient's body and is typically not a part of the electrosurgical instrument itself. In monopolar electrosurgery, the return electrode is part of a device usually referred to as a return pad.

Ablation is a monopolar procedure which is particularly useful in the field of neurosurgery and cancer tumor hyperthermia, where one or more RF ablation needle electrodes (usually of elongated cylindrical geometry) are inserted into a living body. A typical form of such needle electrodes incorporates an insulated sheath from which an exposed (uninsulated) tip extends. When RF energy is provided between the return electrode and the inserted ablation electrode, RF current flows from the needle electrode through the body. Typically, the current density is very high near the tip of the needle electrode, which tends to heat and destroy surrounding tissue.

In bipolar electrosurgery, the return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

SUMMARY

In one embodiment of the present disclosure, an electrosurgical generator is adapted to supply the energy to the at least one active electrode. The electrosurgical generator includes an RF output stage, a DC blocking capacitor, a measuring circuit, and a sensor circuit. The RF output stage generates the electrosurgical energy. The DC blocking capacitor is electrically coupled between the RF output stage and tissue. The electrosurgical generator can detect a fault of the DC blocking capacitor. The measuring circuit is coupled to the DC blocking capacitor and measures the voltage across the DC blocking capacitor. The sensor circuit determines the current of the electrosurgical energy as a function of the voltage across the DC blocking capacitor. In some embodiments of the present disclosure, the system determines the current of the electrosurgical energy in an absence of a current sense transformer to measure the current of the electrosurgical energy. Any of the embodiments disclosed herein of the electrosrugical generator may be used with an electrosurgical system. In an embodiment of the present disclosure, the electrosurgical generator may be used with an electrosurgical system that includes an electrosurgical instrument and the electrosurgical generator. The electrosurgical instrument includes at least one active electrode adapted to apply electrosurgical energy to tissue.

In an embodiment of the present disclosure, the generator further includes a first, second, third, and fourth capacitor. The DC blocking capacitor has first and second nodes and each of the first, second, third, and fourth capacitors has respective first and second nodes. The first capacitor's first node is coupled to the first node of the DC blocking capacitor. The second capacitor's first node is coupled between the second node of the first capacitor and a reference (e.g., ground). The third capacitor's first node is coupled to the second node of the DC blocking capacitor. The fourth capacitor's first node is coupled between the second node of the third capacitor and the reference. The sensor circuit may be coupled to the second node of the first capacitor and the second node of the third capacitor to determine the voltage therebetween to determine the current of the electrosurgical energy as a function of the voltage across the DC blocking capacitor.

In one embodiment of the present disclosure, the first capacitor has a capacitance that is about equal to a capacitance of the third capacitor. The second capacitor may have a capacitance that is about equal to the capacitance of the fourth capacitor.

In yet another embodiment of the present disclosure, the sensor circuit determines the current utilizing the relationship of: I=C(dv/dt). C is an estimated capacitance of the DC blocking capacitor, dv is the measure of the voltage across the DC blocking capacitor, and dt is a predetermined interval of the electrosurgical energy. The DC blocking capacitor may have a capacitance of around 50 nF for bipolar energy and 5 nF for monopolar energy.

In another embodiment of the present disclosure, an electrosurgical generator includes an RF output stage, a DC blocking capacitor, and measuring and sensor circuits. The RF output stage generates electrosrugical energy for application to an active electrode. The DC blocking capacitor is electrically coupled between the RF output stage and the active electrode. The measuring circuit is coupled to the DC blocking capacitor to measure the voltage across the DC blocking capacitor. The sensor circuit determines the current of the electrosurgical energy as a function of the voltage across the DC blocking capacitor.

In an embodiment of the present disclosure, the electrosurgical generator includes fifth and sixth capacitors. The fifth capacitor is connected in series or in parallel with the first capacitor. The sixth capacitor is connected in series or in parallel with the third capacitor.

In another embodiment of the present disclosure, the electrosurgical generator includes a cut-off circuit. The cut-off circuit is coupled to the sensor circuit to communicate the determined current of the electrosurgical therefrom, wherein the cut-off circuit is adapted to stop the application of the electrosurgical energy to the active electrode when the measured current reaches a predetermined threshold. The electrosurgical generator may further include a switch coupled between the RF output stage and the active electrode. The cut-off circuit includes a comparator to compare the determined current to the predetermined threshold and to generate a cut-off signal adapted to signal the switch to stop the application of the electrosurgical energy to the active electrode.

In an embodiment of the present disclosure, a return electrode is adapted to return the electrosurgical energy. An another DC blocking capacitor is electrically coupled between the RF output stage and the return electrode. An another measuring circuit is coupled to the another DC blocking capacitor to measure the voltage across the another DC blocking capacitor. The sensor circuit determines the current of the return electrosurgical energy as a function of the voltage across the another DC blocking capacitor. A leakage current measuring circuit is coupled to the sensor to compare the current of the electrosurgical energy to the current of the return electrosurgical energy to measure a leakage current.

BRIEF DESCRIPTION OF THE DRAWINGS

Various embodiments of the present disclosure are described herein with reference to the drawings wherein.

DETAILED DESCRIPTION

Figure 1:
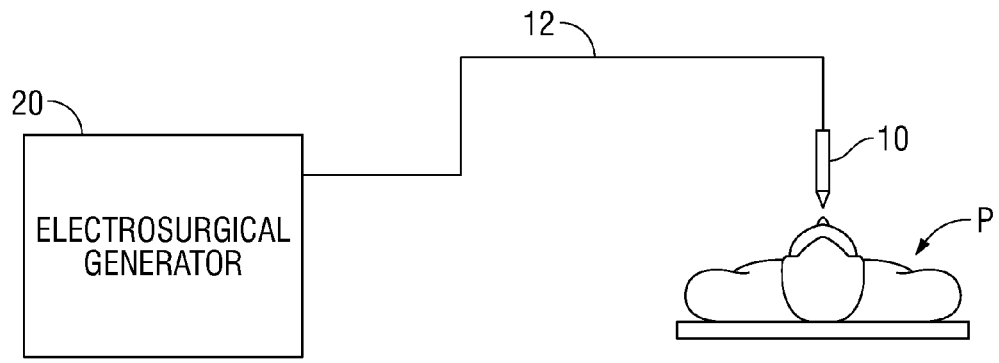
FIG. 1 is a schematic block diagram of an electrosurgical system according to the present disclosure.

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems. FIG. 1 is a schematic illustration of an electrosurgical system according to the present disclosure. The system includes an electrosurgical instrument 10 having one or more electrodes for treating tissue of a patient P. The instrument 10 may be either of monopolar type including one or more active electrodes (e.g., electrosurgical cutting probe, ablation electrode(s), etc.) or of bipolar type including one or more active and return electrodes (e.g., electrosurgical sealing forceps). Electrosurgical RF energy is supplied to the instrument 10 by a generator 20 via a supply line 12, which is operably connected to an active output terminal, allowing the instrument 10 to coagulate, seal, ablate and/or otherwise treat tissue.

If the instrument 10 is of monopolar type then energy may be returned to the generator 20 through a return electrode (not explicitly shown) which may be one or more electrode pads disposed on the patient's body. The system may include a plurality of return electrodes which are believed to minimize the chances of tissue damage by maximizing the overall contact area with the patient P. In addition, the generator 20 and the monopolar return electrode may be configured for monitoring the sufficiency of the so called "tissue-to-patient" contact impedance to further minimize chances of tissue damage.

If the instrument 10 is of bipolar type, the return electrode is disposed in proximity to the active electrode (e.g., on opposing jaws of bipolar forceps). The generator 20 may include a plurality of supply and return terminals and a corresponding number of electrode leads.

The generator 20 includes input controls (e.g., buttons, activators, switches, touch screen, etc.) for controlling the generator 20. In addition, the generator 20 may include one or more display screens for providing the surgeon with variety of output information (e.g., intensity settings, treatment complete indicators, etc.). The controls allow the surgeon to adjust power of the RF energy, waveform, and other parameters to achieve a waveform suitable for a particular task (e.g., coagulating, tissue sealing, intensity setting, etc.). The instrument 10 may also include a plurality of input controls redundant with certain input controls of the generator 20. Redundant input controls on the instrument 10 allow for easier and faster modification of RF energy parameters during the surgical procedure without requiring interaction with the generator 20.

Figure 2:
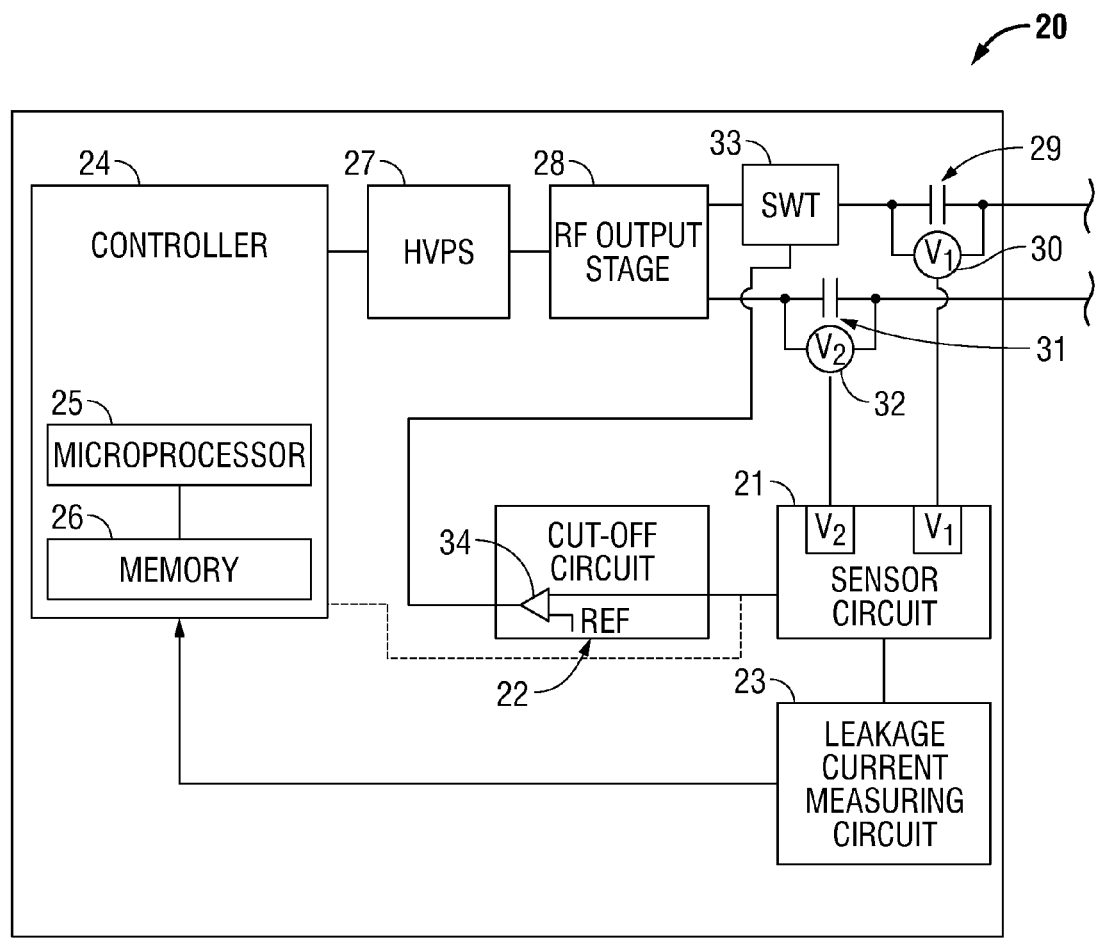
FIG. 2 is a schematic block diagram of an electrosurgical generator according to the present disclosure.

FIG. 2 shows a schematic block diagram of the generator 20 having a sensor circuit 21, a cut-off circuit 22, a leakage current measuring circuit 23, a controller 24, a high voltage DC power supply 27 ("HVPS") and an RF output stage 28. The HVPS 27 provides high voltage DC power to an RF output stage 28 which then converts high voltage DC power into RF energy and delivers the RF energy to the active electrode of the instrument 10. In particular, the RF output stage 28 generates sinusoidal waveforms of high frequency RF energy. The RF output stage 28 is configured to generate a plurality of waveforms having various duty cycles, peak voltages, crest factors, and other parameters. Certain types of waveforms are suitable for specific electrosurgical modes. For instance, the RF output stage 28 generates a 100% duty cycle sinusoidal waveform in cut mode, which is best suited for dissecting tissue, and a 25% duty cycle waveform in coagulation mode, which is best used for cauterizing tissue to stop bleeding.

The controller 24 includes a microprocessor 25 operably connected to a memory 26 that may be volatile type memory (e.g., RAM) and/or non-volatile type memory (e.g., flash media, disk media, etc.). The microprocessor 25 includes an output port that is operably connected to the HVPS 27 and/or the RF output stage 28 allowing the microprocessor 25 to control the output of the generator 20 according to either open and/or closed control loop schemes.

A closed loop control scheme is a feedback control loop wherein the sensor circuitry 21, which may include a plurality of sensors measuring a variety of tissue and energy properties (e.g., tissue impedance, tissue temperature, output current and/or voltage, etc.), provides feedback to the controller 24. The controller 24 then signals the HVPS 27 and/or RF output stage 28 which then adjusts the DC and/or the RF power supply, respectively. The controller 24 also receives input signals from the input controls of the generator 20 or the instrument 10. The controller 24 utilizes the input signals to adjust power outputted by the generator 20 and/or perform other control functions thereon.

The DC blocking capacitor 29 provides DC blocking for electrosurgical energy going to an active electrode (not shown). The measuring circuit 30 measures the voltage across the DC blocking capacitor 29 for communication to the sensor circuit 21. The DC blocking capacitor 31 provides DC blocking of return electrosurgical energy. The measuring circuit 32 measures the voltage across the DC blocking capacitor 31. The sensor circuit 21 can determine the current of the electrosurgical energy supplied to the active electrode utilizing the voltage across capacitor 29 and likewise can determine the return current utilizing the voltage across DC blocking capacitor 31. The controller 24 can utilize the voltages and/or the currents through DC blocking capacitors 29 or 31 to detect any faults therein.

The current communicated through DC blocking capacitors 29 or 31 can be determined using voltage measurements obtained from the measuring circuits 30 or 32, respectively. The current through a capacitor may be determined using its voltage by using the following relation (1):

$$I=C(dv/dt), \quad (1)$$

where C is an estimated capacitance of the DC blocking capacitor, dv is the measure of the voltage across the DC blocking capacitor, and dt is a predetermined interval of the electrosurgical energy. The predetermined interval may be the switching interval of the electrosurgical energy.

The sensor circuit 21 communicates the currents to cut-off circuit 22 and/or controller 24. The cut-off circuit 22 can compare the output current to a reference. (e.g., using comparator 34). If the output current exceeds the reference, then the cut-off circuit 22 signals the switch 33 to disconnect the RF output stage from the active electrode (not shown). The leakage current measuring circuit 23 receives the electrosurgical current and return current from the sensor circuit 21. The leakage current measuring circuit 23 determines the leakage current for communication to the controller 24.

Figure 3:
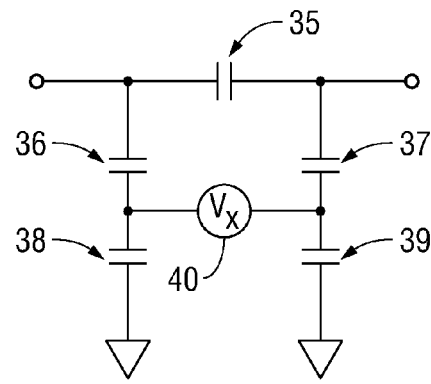
FIG. 3 shows a circuit coupled to a DC blocking capacitor that may be used by the generator of FIG. 1 or 2 according to the present disclosure.

FIG. 3 shows a circuit coupled to a DC blocking capacitor 35 that may be used by the generator of FIGS. 1 and/or 2 according to the present disclosure. FIG. 3 shows the DC blocking capacitor 35 which may be blocking capacitor 29 and/or 31 of FIG. 2. The capacitors 36, 37, 38, and 39 are arranged in an H configuration and function as a divider network. The capacitors 36, 37, 38, and 39 provide an isolation barrier between the patient and the ground of the generator. In some embodiments of the present disclosure, optocouplers and/or isolation transformers are used to provide an isolation barrier between the patient and the ground of the generator; and in other embodiments they are not used. The measuring circuit 40 may be measuring circuit 30 or 32 of FIG. 2. The measuring circuit 40 measures the voltage difference between the nodes of: (1) the node between capacitors 36 and 38, and (2) the node between capacitors 37 and 39. The capacitors 36 and/or 37 may be split into various parallel or serial capacitors to adjust creepage, clearance, and the voltage breakdown for the isolation barrier between the patient and ground. The capacitors 36 and 38 form a divider network. The capacitors 37 and 39 form another divider network. The capacitors 36 and 37 have the same capacitance; and the capacitors 38 and 39 have the same capacitance. The divider network formed by capacitors 36, 37, 38, and 39 reduces the voltage measured by measuring circuit 40 by a predetermined amount and is a function of the frequency of the electrosurgical energy, the capacitance of the capacitors 36, 37, 38 and 39, and the DC blocking capacitor 35. The capacitors 36, 37, 38, and 39 are sufficient to provide isolation between a ground of the electrosurgical generator 20 (See FIG. 1) and the patient P, e.g., to prevent voltage breakdown of the capacitors 36, 37, 38, and 39 during typical use between the patient and a ground of the electrosurgical generator 20.

In some embodiments of the present disclose, a transformer may be interposed between DC blocking capacitor 35 and measuring circuit 40 to provide isolation therebetween and/or to step-down the voltage of the electrosurgical energy prior to measurement by measuring circuit 40.

Figure 4:
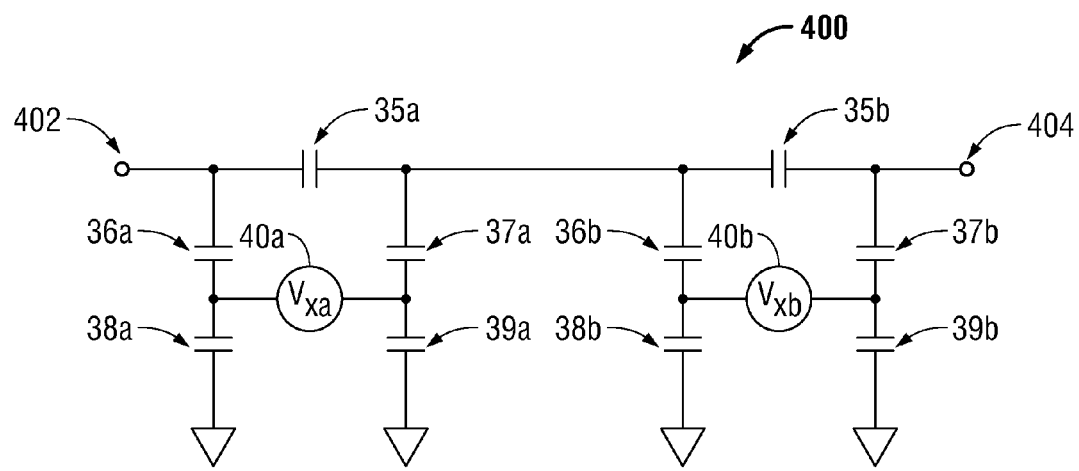
FIG. 4 shows a circuit coupled to a DC blocking capacitor and a redundant DC blocking capacitor for determining the current of the electrosurgical energy according to the present disclosure.

FIG. 4 shows a circuit 400 coupled to a DC blocking capacitor 35a and a redundant DC blocking capacitor 35b for determining the current of the electrosurgical energy according to the present disclosure. Nodes 402 and 404 may be coupled between SWT 33 of FIG. 2 and the active electrode (not shown). For example, the blocking capacitors 35a and 35b may be used in place of or in addition to capacitor 29 of FIG. 2. The circuit 400 includes the measuring circuits 40a and 40b. The measuring circuit 40a measures the voltage across the DC blocking capacitor 35a using the capacitors 36a, 37a, 38a and 39a. The measuring circuit 40b measures the voltage across the DC blocking capacitor 35a using the capacitors 36a, 37a, 38a, and 39a. The blocking capacitors 35a and 35b provide redundant electrosurgical energy measurements.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator comprising:
   an RF output stage adapted to generate electrosurgical energy, supply the electrosurgical energy to an output port through an active line, and receive return electrosurgical energy from the output port through a return line;
   a first direct current (DC) blocking capacitor electrically coupled between the RF output stage and the output port along the active line;
   a second DC blocking capacitor electrically coupled between the RF output stage and the output port along the return line;
   a first sense circuit to detect a first voltage of the electrosurgical energy generated by the RF output stage across the first DC blocking capacitor;
   a second sense circuit to detect a second voltage of the return electrosurgical energy across the second DC blocking capacitor;
   a cut-off circuit coupled to a sense circuit, the cut-off circuit including a comparator for comparing an output current to a predetermined threshold and generating a cut-off signal; and
   a switch, which upon receiving the cut-off signal opens and prevents the RF output stage from supplying the electrosurgical energy to the output port,
   wherein the output current is based on the first voltage and the second voltage.

2. The electrosurgical generator according to claim 1, wherein one or more electrosurgical instruments are connectable to the output port.

3. The electrosurgical generator according to claim 1, wherein the switch is coupled between the RF output stage and the output port along the active line.

4. The electrosurgical generator according to claim 1, further comprising:

a first capacitor having a first node coupled to a first node of the first DC blocking capacitor; and a second capacitor having a first node coupled between a second node of the first capacitor and a reference.

5. The electrosurgical generator according to claim 4, further comprising:

a third capacitor having a first node coupled to a second node of the first DC blocking capacitor; and a fourth capacitor having a first node coupled between a second node of the third capacitor and the reference.

6. The electrosurgical generator according to claim 5, wherein the first sense circuit is coupled to the second node of the first capacitor and the second node of the third capacitor to determine the first voltage and to determine a first current of the electrosurgical energy based on the first voltage across the first DC blocking capacitor.

7. The electrosurgical generator according to claim 1, wherein the first sense circuit determines a first current of the electrosurgical energy in an absence of a current sense transformer.

8. The electrosurgical generator according to claim 1, further comprising:

a first capacitor having a first node coupled to a first node of the second DC blocking capacitor; and a second capacitor having a first node coupled between a second node of the first capacitor and a reference.

9. The electrosurgical generator according to claim 8, further comprising:

a third capacitor having a first node coupled to a second node of the second DC blocking capacitor; and a fourth capacitor having a first node coupled between a second node of the third capacitor and the reference.

10. The electrosurgical generator according to claim 9, wherein the second sense circuit is coupled to the second node of the first capacitor and the second node of the third capacitor to determine the second voltage and to determine a second current of the return electrosurgical energy based on the second voltage across the second DC blocking capacitor.

11. The electrosurgical generator according to claim 1, wherein the second sense circuit determines a second current of the return electrosurgical energy in an absence of a current sense transformer.

12. The electrosurgical generator according to claim 1, wherein the first sense circuit is configured to determine a first current of the electrosurgical energy passing through the first DC blocking capacitor.

13. The electrosurgical generator according to claim 12, wherein the second sense circuit is configured to determine a second current of the return electrosurgical energy passing through the second DC blocking capacitor.

14. The electrosurgical generator according to claim 13, wherein the output current is based on the first current and the second current.

15. The electrosurgical generator according to claim 13, further comprising a leakage current measuring circuit configured to determine a leakage current based on the first current and the second current.

* * * * *

UNITED STATES PATENT AND TRADEMARK OFFICE
CERTIFICATE OF CORRECTION

| | |
|---|---|
| PATENT NO. | : 9,987,069 B2 |
| APPLICATION NO. | : 14/692249 |
| DATED | : June 5, 2018 |
| INVENTOR(S) | : Behnke et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this
Thirteenth Day of December, 2022

Katherine Kelly Vidal
*Director of the United States Patent and Trademark Office*